United States Patent [19]
Zohmann

[11] Patent Number: 5,449,351
[45] Date of Patent: Sep. 12, 1995

[54] ATRAUMATIC NEEDLE FOR LUMBAR PUNCTURE

[76] Inventor: Walter A. Zohmann, P.O. Box 681180/528 Park Ave., Park City, Utah 84068-1180

[21] Appl. No.: 118,870

[22] Filed: Sep. 9, 1993

[51] Int. Cl.$^6$ .............................................. A61M 5/32
[52] U.S. Cl. .................................. 604/272; 604/158; 604/274
[58] Field of Search .......................... 606/222–224; 163/5; 604/272, 274, 264, 158; 64/272, 264, 274

[56] References Cited

U.S. PATENT DOCUMENTS

| | | | |
|---|---|---|---|
| 2,748,769 | 6/1956 | Huber | 604/272 |
| 4,808,157 | 2/1989 | Coombs | 604/272 |
| 4,838,877 | 6/1989 | Massau | 604/272 |
| 5,100,390 | 3/1992 | Lubeck et al. | 604/274 |

FOREIGN PATENT DOCUMENTS 2654486  6/1977  Germany ..................... 163/5

*Primary Examiner*—Gary Jackson
*Attorney, Agent, or Firm*—J. Winslow Young

[57] ABSTRACT

An elongated, hollow spinal needle that is less prone to causing postdural puncture headache by having a modified, pencil-like point with a rounded shoulder at the juncture between the modified, pencil-like point and the body of the spinal needle. A side port is formed in the hollow needle at a position adjacent the rounded shoulder. The leading edge of the side port is located not more than 1.5 times the external diameter of the hollow needle from the tip of the pencil-like point to reduce the bending moment between the tip and the side port. The cross sectional area of the side port is configured to be equal to or incrementally larger than the cross sectional area of the lumen of the hollow needle.

8 Claims, 2 Drawing Sheets

ATRAUMATIC NEEDLE FOR LUMBAR PUNCTURE

BACKGROUND

1. Field of the Invention

This invention relates to needles for use in performing lumbar puncture procedures and, more particularly, to a novel, atraumatic needle apparatus and method for significantly reducing postdural puncture headaches.

2. The Prior Art

Spinal anesthesia is one of the most frequently employed methods of regional anesthesia. This regional anesthesia is accomplished by the temporary interruption of nerve transmission using a local anesthetic injected into the readily identifiable subarachnoid space. The ensuing anesthesia is predictable, occurs rapidly, and is associated with profound muscle relaxation. The patient may be wide awake, or if preferred, the anesthetic may be supplemented with varying amounts of sedative-tranquilizers. Spinal anesthesia is particularly useful for surgery involving the lower extremities, pelvis, perineum, and lower abdomen.

The spinal column, which surrounds the spinal cord, is formed by a series of vertebrae separated by cartilaginous intervertebral disks and united by a series of ligaments. The body of each vertebra bears the weight of the patient and forms the base of the neural arch. The arch, which surrounds the spinal cord, is made up of a pedicle and lamina on each side. Between the laminae of each vertebra there is a posterior opening in the vertebral canal. It is through this opening that a spinal needle is passed when performing a subarachnoid block.

In adults the spinal cord varies in length from 40 to 45 cm. and ends at various levels of the vertebral column depending on the age of the patient. In the newborn, the spinal cord extends to the third lumbar vertebra, but in the adult it usually ends at the lower border of the first lumbar vertebra because the spinal cord does not grow as much as the vertebral column. Thirty-one pairs of symmetrically arranged spinal nerves are each attached to the spinal cord by an anterior and posterior root. Because the spinal cord is shorter than the vertebral column, the spinal cord segments in adults do not lie opposite their corresponding vertebrae. The spinal nerve roots must travel obliquely in a caudad direction to reach their respective intervertebral foramina. The roots of the lumbar, sacral, and coccygeal nerves comprise the cauda equina and are necessarily the largest and longest in order to reach their intervertebral foramen. The greater size of these nerve roots provides a larger surface area to be exposed to the action of local anesthetics, thus allowing more rapid onset of anesthesia.

The spinal cord is covered by three membranes or meninges. The dura mater (the outermost membrane) is the downward continuation of the meningeal layer of the cranial dura mater. The middle of the three coverings, the arachnoid is a thin membrane closely adherent to the dura mater. The dura and the arachnoid are in such close contact that usually it is not possible to puncture the dura without also piercing the arachnoid. Nevertheless, on rare occasions, the tip of the conventional epidural or spinal needle may accidentally enter the subdural space. Local anesthetic inadvertently injected into the subdural space will diffuse poorly and result in inadequate contact with the nerve roots. Poor or absent anesthesia may ensue. Should subdural placement occur during an attempted epidural anesthetic, the improper position of the needle may not be recognized and the injection of an epidural dose of local anesthetic may result in a much higher block than anticipated.

The innermost membrane, the pia mater, is a thin, delicate, highly vascular membrane closely adherent to the spinal cord. The space surrounding the pia is filled with cerebrospinal fluid and is enclosed externally by the arachnoid. In addition to spinal fluid, this space contains the spinal nerve roots and the main blood vessels of the central nervous system. In the cervical and thoracic regions, the space is only about 3 mm deep, but below the lower border of the first lumbar vertebra, where the spinal cord usually ends, the space has a diameter of about 14 to 15 mm.

A spinal needle 9 cm long is usually adequate, but longer ones (10–15 cm) are available for the occasional obese patient or difficult paramedian approach. A removable, close-fitting stylet helps stiffen the needle and prevents coring of the tissue. Commonly, two sizes of spinal needles are used, 22 gauge and 25 gauge. The larger diameter 22 gauge needle is easier to direct and renders the characteristic feel of the various ligaments penetrated easier to appreciate. However, the incidence of postspinal headache is increased with the larger needle, particularly if the larger needle is also equipped with a standard point which is a cutting bevel.

A postdural puncture headache is the most common postoperative complication of spinal anesthesia. The incidence increases with the larger spinal needles and those with a cutting bevel at the tip but decreases with increasing patient age. Postdural puncture headache also occurs more commonly in women than in men, and more often in pregnant women than in nonpregnant women. The headache is positional in that it comes on in the upright position and is relieved or at least improved in the recumbent position.

The causative mechanism of the postdural puncture headache is believed to be associated with the continuing leakage of cerebrospinal fluid (CSF) through the dural opening left by the spinal needle. The leakage of CSF causes a decrease in CSF pressure which, in turn, produces compensatory cerebral vasodilation. Bringing the patient into the erect position also results in traction on the pain-sensitive, dilated blood vessels. Accordingly, conservative therapy for the postdural puncture headache consists of bed rest and analgesics.

Various preventive measures for the postdural puncture headache have been advocated. The common practice of keeping the patient supine for 4 to 24 hours after lumbar puncture has been shown to be ineffective. For a standard point needle having a cutting bevel at its tip, insertion of the needle with the bevel parallel to the longitudinal fibers of the dura appears to produce a smaller rent in the dura with a lower incidence of headache. Pencil point needles such as the commercially available Whitacre and Sprotte needles also have a lower incidence of headaches. These pencil-point needles have a closed pencil point created when the open end of the needle is swaged closed, as the name implies, like a pencil point or, more accurately, with a conical apex. This conical apex is believed to spread, rather than cut, the predominately longitudinal dural fibers and, on removal of the needle, the resulting dural hole should be smaller and seal off more rapidly. Indeed, studies have shown that the incidence of postspinal headache when a 22 gauge conical apex needle is used is comparable to that following use of the much smaller 26 gauge, bevel needle.

In an attempt to suitably occlude the dural opening to minimize leakage of CSF, an available procedure is to create what is known as a blood patch. This is done by obtaining 10 to 20 cc of blood from the patient and injecting this volume of blood into the tissue adjacent the puncture site of the spinal needle. This relatively large volume of blood is required since it is virtually impossible for the health care professional to exactly position the blood patch directly over the original puncture site. In effect, therefore, the blood patch is designed to seal the dural puncture thereby significantly minimizing the frequency of the postdural headache.

However, even with these improvements, postdural puncture headache remains a problem although the frequency is significantly reduced. Further, an adequate flow rate of anesthetic through the smaller needle is also a concern particularly with the pencil-point or conical-apex needle since the injection is through a side port located an incremental distance behind the tip. The placement and size of this side port is an important feature since it affects both the distribution of the anesthetic as well as overall strength of the needle. One particular needle (Sprotte, see FIG. 1, Prior Art) has a relatively long side port which has been found in certain circumstances to deliver anesthetic to both sides of the dura since the length of the side port is greater than the thickness of the dura. Another prior art needle (Whitacre) has a shorter side port but is cut wider across the needle to overcome this shortcoming. A wider side port, however, weakens the needle particularly if the side port is any appreciable distance from the pencil-point tip.

Another disadvantage to the presently available pencil-point-tip spinal needles is that the sides of the tip are generally straight in a true cone configuration. Thus, a relatively abrupt shoulder is formed as a ridge at the juncture between the sloped sides of the conical tip and the cylindrical side walls of the body of the needle. It is currently postulated that this relatively abrupt change in the profile of the needle excessively distorts the dura and thereby contributes to the presence of a post puncture hole in the dura.

In view of the foregoing, it would be an advancement in the art to provide a spinal needle having a pencil-like point with a gently rounded profile to reduce the trauma to the fibers of the dura. It would also be an advancement in the art to provide a spinal needle of which the side port has an opening with a cross sectional area only incrementally larger than the cross sectional area of the lumen of the hollow needle. It would also be an advancement in the art to provide a spinal needle having a side port immediately adjacent the pencil-like point thereby reducing the length of the moment arm between the tip of the pencil-like point and the midline of the side port. Such a novel spinal needle is disclosed and claimed herein.

BRIEF SUMMARY AND OBJECTS OF THE INVENTION

This invention is an atraumatic spinal needle apparatus and method wherein the needle is provided with a gently curved, pencil-like point and a side port immediately distal the pencil-like point. The sides of the pencil-like point are gently rounded to enable the point to part the fibers of the dura with minimal trauma. The side port has a cross sectional area incrementally larger than the cross sectional area of the lumen of the hollow needle and is located immediately adjacent the pencil-like point in order to reduce the length of the moment arm between the tip of the pencil-like point and the midline of the side port. All corners and edges in contact with the dura, with the exception of the tip of the pencil-like point, are smoothly rounded to reduce trauma to the dura.

It is, therefore, a primary object of this invention to provide improvements in spinal needle apparatus.

Another object of this invention is to provide improvements in the method of delivering an anesthetic with a spinal needle.

Another object of this invention is to provide a spinal needle with a pencil-like point having gently rounded sides where the point joins the cylindrical sidewall of the needle shaft.

Another object of this invention is to provide a spinal needle having a side port immediately adjacent the pencil-like point.

Another object of this invention is to provide a side port to a spinal needle, the side port having a cross sectional area that is incrementally larger than the cross sectional area of the lumen of the spinal needle.

These and other objects and features of the present invention will become more readily apparent from the following description in which preferred and other embodiments of the invention have been set forth in conjunction with the accompanying drawing and appended claims.

DETAILED DESCRIPTION OF THE PREFERRED EMBODIMENTS

Figure 1:
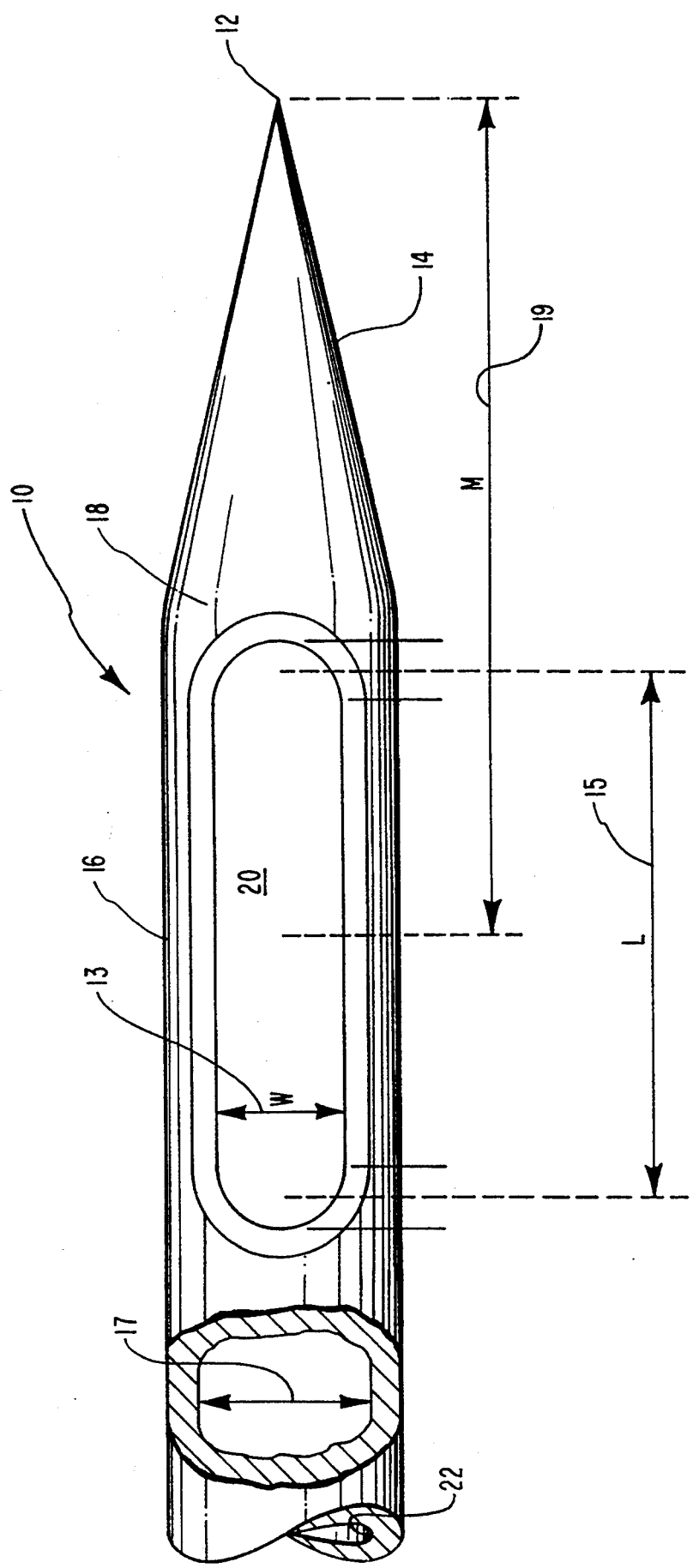
FIG. 1 is an enlarged, plan view of the tip of a prior art spinal needle shown with portions broken away for ease of illustration of internal features.

The invention is best understood by the following description with reference to the drawing wherein like parts are designated by like numerals throughout.

General Discussion

The spinal needle of the present invention has a modified, pencil-like point and a side port immediately adjacent the shoulder portion of the modified, pencil-like point. The term "modified, pencil-like point" is used herein to distinguish the shape of the sharpened tip of the spinal needle of this invention from that of the conventional spinal needle. Conventional pencil points are constructed as the surface of a right circular cone wherein the sharpened tip has generally straight, conical sidewalls that define the surface of the pencil point. This straight sidewall, in turn, joins the cylindrical surface of the body of the needle in a relatively abrupt corner formed circumferentially adjacent the needle tip at the juncture between the pencil point and the needle body.

Referring specifically to FIG. 1 (Prior Art) a portion of the pointed end of a conventional spinal needle is shown generally at 10 (greatly enlarged) and includes a tip 12, having straight, conical sidewalls 14, a cylindrical needle body 16, and a side port 20. The juncture between straight, conical sidewall 14 and cylindrical needle body 16 is shown as a relatively abrupt ridge or shoulder 18. The theory behind using this type of pencil-point needle is that tip 12 is more likely to forcibly part the fibers of the dura rather than cut them thus leaving a smaller hole that can be sealed off more readily after the needle has been withdrawn. However, it is postulated that excessive stretching and even a limited amount of tearing of the dura occurs when shoulder 18 is forced through the dura with the result that a hole of sorts remains in the dura upon withdrawal of the needle. It is this hole that is believed to be responsible for the post puncture headaches that have been recorded when using the foregoing pencil-point spinal needles.

On certain occasions, it has also been found that the location and relative length of side port 20 will result in its being positioned such that it transects the dura so that a portion of the anesthetic is delivered on both surfaces of the dura. In effect, side port 20 is too large in that it occupies too much distance along the axial length of spinal needle 10. This excessive length of side port 20 appears to be a compromise between cutting away too much external wall of spinal needle 10 while at the same time providing sufficient area to side port 20 to assure adequate flow of anesthetic through side port 20.

Regrettably, this compromise has created the foregoing problem of straddling of the dura. Further, the placement of side port 20 distally from shoulder 18 produces a resulting moment arm 19 represented by the distance between tip 16 and the midline of side port 20. Moment arm 19 becomes important when tip 16 strikes bone or is otherwise deflected resulting in a bending force being imposed on the tip of spinal needle 10. This bending force is multiplied by the distance through which moment arm 19 can act, namely, the distance between tip 16 and side port 20. Accordingly, if spinal needle 10 is going to bend, it will bend at the midline of side port 20 because of the force of the bending moment exerted on moment arm 19 coupled with the fact that the presence of side port 20 significantly reduces the overall mass of spinal needle 10 at that particular location.

The size or cross sectional area of side port 20 of this prior art needle 10 is too large in that the extraneous cross sectional area contributes nothing to the adequate delivery of anesthetic through needle 10. In particular, the anesthetic solution is a liquid and is therefore non-compressible so that the rate of flow through prior art needle 10 is a function of the pressure exerted on the anesthetic solution, the viscosity of the anesthetic solution, and the cross sectional area of the lumen of prior art needle 10. Only if the cross sectional area of side port 20 is less than that of lumen 22 will it have an adverse affect on the rate of flow of the anesthetic solution. This is because the limiting factor for a non-compressible fluid will inherently be the cross sectional area of the lumen, not the cross sectional area of side port 20, particularly if this latter cross sectional area is significantly larger than the cross sectional area of the lumen.

Accordingly, simply providing an oversize side port 20 that has a cross sectional area that is two or three times larger than the cross sectional area of the lumen provides no improvement in the flow of the anesthetic solution through prior art needle 10. Instead, the oversize side port 20 represents a source of a potential hazard in that the oversize side port 20 removes material from the side walls of prior art needle 10 which, in turn, drastically reduces the mechanical strength of the prior art needle 10 particularly as it relates to the residual side walls adjacent side port 20 and the length of moment arm 19 represented by the distance between the midline of side port 20 and tip 16. This latter consideration is important in the event pencil point or tip 16 strikes a bone causing tip 16 to be deflected creating a bending moment against tip 16 through moment arm 19. If side port 20 is oversized, this bending moment could cause prior art needle 10 to bend at its weakest point which will inherently be across the midsection of side port 20 where the sidewall mass is at a minimal amount.

The negligible advantage provided by the larger cross sectional area of side port 20 was confirmed by a carefully conducted experiment. In this experiment the size of side port 20 was measured along with the cross sectional area of lumen 22 of prior art spinal needle 10. The prior art spinal needle 10 selected for this study was a 24 g Sprotte-PAJUNK needle. The internal diameter 17 was measured by a micrometer and was found to be 0.35 mm. The length 15 and width 13 of side port 20 were found to be 1.7 mm and 0.32 mm, respectively. Accordingly, the cross sectional area of lumen 22 was calculated to be 0.096 $mm^2$ while the cross sectional area of side port 20 was calculated to be 0.544 $mm^2$ which is over five times the cross sectional area of lumen 22 of prior art spinal needle 10. Clearly, of course, the internal diameter 17 is the most important factor affecting the flow rate so that there is absolutely no benefit in having a side port 20 having an area significantly larger than the cross sectional area of lumen 22.

This same prior art spinal needle 10 was then modified by reducing the area of side port 20 to an area approximately equal to the cross sectional area of lumen 22. It was found that there was no difference in the measured flow through either needle. This study was reported by Aglan, M. Y. and Stansby, P. K. in *Anaesthesia*, 1992, Volume 47, pp 506–507.

Detailed Description

Figure 2:
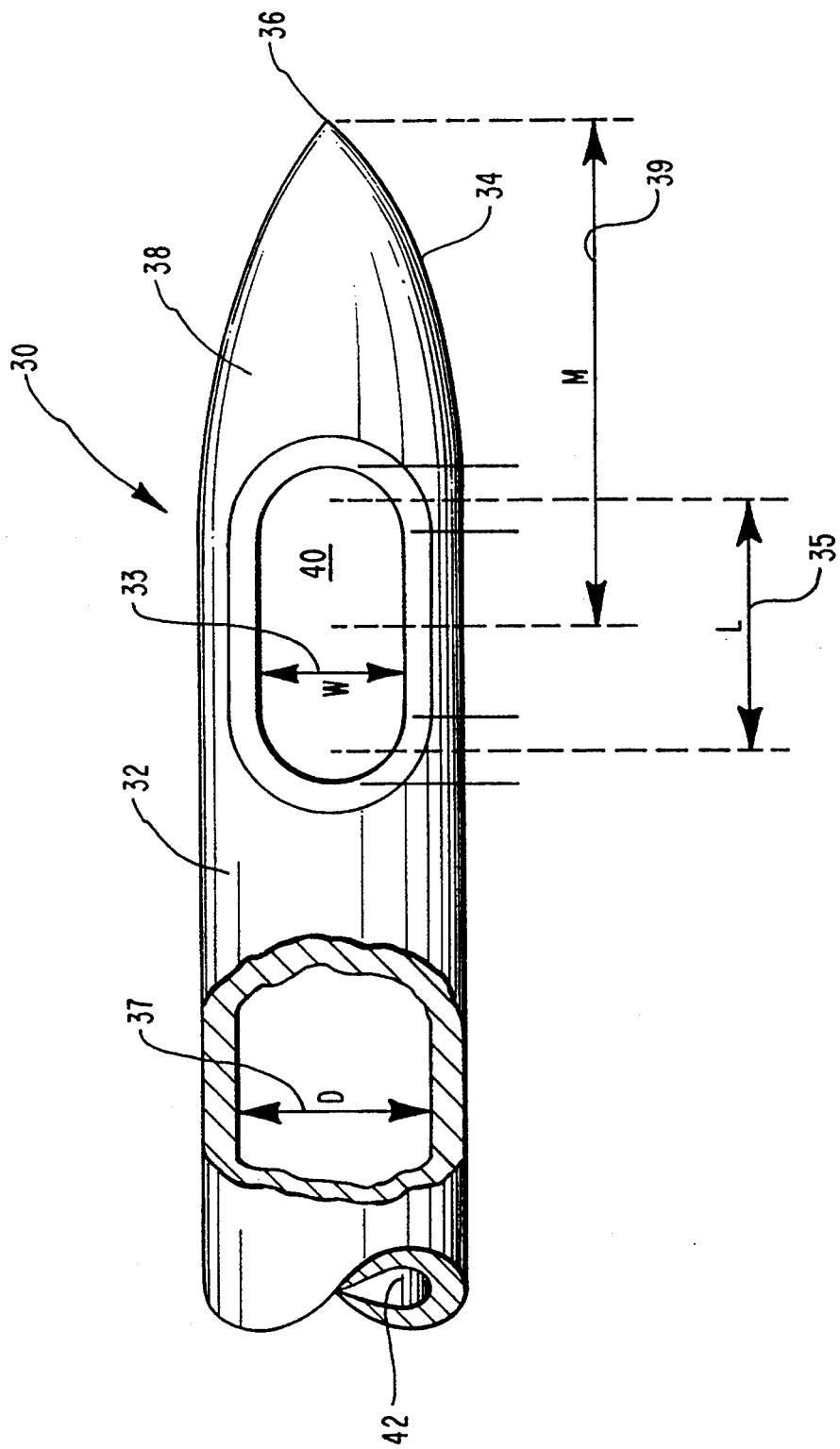
FIG. 2 is an enlarged, plan view of the tip of the novel atraumatic needle for lumbar puncture of this invention shown with portions broken away for ease of illustration of internal features.

Referring now to FIG. 2, the novel spinal needle of this invention is shown generally at 30 and includes a needle body 32 having a rounded point 34 terminating in a sharpened tip 36. The transition zone where the external surface of needle body 32 transitions to rounded point 34 is shown as shoulder 38. A side port 40 having a width 33 and a length 35 is located adjacent shoulder 38. Interiorly, spinal needle 30 has a hollow lumen 42 having an inside diameter 37.

The cross sectional area of lumen 42 is determined by the well-known mathematical formula for the area of a circle having a diameter equal to that of inside diameter 37. Accordingly, it is this area that is the critical factor for flow of anesthetic solution (not shown) through lumen 42 as long as the area of side port 40 is at least equal to or greater than the cross sectional area of lumen 42. In this presently preferred embodiment of this invention, the relationship of the area of side port 40 to the cross sectional area of lumen 42 is assured by forming length 35 of side port 40 as one and a half times inside diameter 37 of lumen 42. For example, if inside diameter 37 is 0.027 inches (0.686 mm) for a 26 gauge spinal needle 30, then length 35 of side port 40 will be 0.0405 inches (1.029 mm). The spinal needle 30 having a gauge size preferable between 20 and 26 gauge.

At this point it should be pointed out that the area or, more particularly, the length 35 of side port 40 is shown at its maximum which is 1.5 times inside diameter 37. Clearly, therefore, in actual production, spinal needle 30 will have a side port 40 that has a length 35 that is incrementally less than 1.5 times the internal diameter 37 so long as the resultant area of side port 40 is equal to or incrementally larger than the cross sectional area of lumen 42. The mathematical formula representing this relationship is as follows:

$$L \times W \cong \frac{\pi D^2}{4}$$

Where L is length 35 and W is width 33.

The juncture between rounded point 34 and needle body 32 is configured as a gently rounded shoulder 38 having a very gradual change in overall dimension diametrally as a function of length thereby substantially reducing any tendency for a sharp change in dimension (in contrast, see ridge 18, FIG. 1, PRIOR ART). Thus, any tendency for shoulder 38 to excessively stretch or otherwise tear the fibers of the dura (not shown) is significantly reduced. This feature is important not only during penetration but also upon withdrawal of spinal needle 30 from the dura. In particular, the fibers of the dura inherently have a certain degree of elasticity so that they can be stretched to a limited degree by the penetration of spinal needle 30. The smooth profile of rounded point 34 in combination with the rounded, gentle profile of shoulder 38 allows the fibers of the dura sufficient time to stretch adequately to allow the passage of spinal needle 30 without exceeding the relatively limited elastic limit of the fibers of the dura.

Importantly and advantageously, I have found that my novel spinal needle 30 substantially eliminates the residual hole in the dura and, therefore, the need for the health care professional to create a blood patch adjacent the place of exit of needle 30 from the dura (not shown). This surprising result is the direct consequence of the gentle profile of shoulder 38 which gently parts the fibers of the dura without cutting them or otherwise damaging them to the extent that a postdural headache does not develop as in the case of prior art needle 10 (FIG. 1).

Tip breakage of spinal needle 30 is an extremely important consideration particularly when one considers the inherent danger of rounded point 34 breaking off in the immediate vicinity of the spinal cord (not shown). For this reason moment arm 39, as measured between the midline of side port 40 and tip 36, is kept as short as possible consistent with the need to have sufficient length to rounded point 34 to accommodate parting of the fibers of the dura as discussed previously. In this presently preferred embodiment the length of moment arm 39 is held within desirable limits by placing the leading edge of side port 40 at a position from tip 36 not to exceed 1.5 times the outside diameter of spinal needle 30.

This placement of side port 40 also provides the advantage of having the leading edge of side port 40 in the close vicinity of the curvature region of shoulder 38 thereby incrementally modifying the total external profile of spinal needle 30 at shoulder 38 as shoulder 38 passes into the dura (not shown).

The Method

Spinal needle 30 is configured with a conventional needle hub (not shown) and is used in the conventional manner to introduce the appropriate quantity of anesthetic intrathecal space of the dura. Importantly, tip 36 along with the gentle profile of rounded point 34 and shoulder 38 parts the fibers of the dura (not shown) without cutting, excessively stretching, or otherwise tearing the same. Accordingly, after spinal needle 30 is withdrawn the fibers of the dura are able to return to their original position thereby closing the hole to preclude excessive leakage of the CSF.

From the foregoing, the most important aspect of spinal needle 30 is not what it is but what it virtually eliminates, usually the creation of a postdural headache after spinal needle 30 has been withdrawn. This means that the medical professional is required to spend less time since he/she is able to quickly and easily inject the appropriate quantity of anesthetic and then remove spinal needle 30. Further, the anesthetic is delivered more efficiently since side part 40 occupies less distance along the length of spinal needle 30 thereby effectively eliminating the risk of delivery of anesthetic on both sides of the dura.

Spinal needle 30 is also safer to use due to the close proximity of side part 40 to tip 36 resulting in a foreshortened moment arm 39. Thus, in the event a bone (not shown) is struck by tip 36, the shorter length of moment arm 39 means that a substantially greater force will be required to be imposed against moment arm 39 in order to create a bending action against the end of spinal needle 30. A force of sufficient magnitude to create a bending action in prior art needle 10 will not affect spinal needle 30.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An improved spinal needle for the delivery of an anesthetic to the subdura, said improved spinal needle being configured as an elongated, hollow needle having a lumen, said lumen having a first cross sectional area, the improvement comprising:
   a relatively small gauge for said hollow needle, said relatively small gauge comprising a needle gauge that is at least as small as 24 gauge;
   a modified pencil-like point on a distal end of said elongated, hollow needle;
   a rounded shoulder circumscribing said elongated, hollow needle at the juncture of said modified pencil-like point and said elongated, hollow needle;
   a side port in said elongated, hollow needle, said side port being located adjacent said rounded shoulder and having a second cross sectional area, said second cross sectional area being incrementally larger than said first cross sectional area of said lumen of said elongated, hollow needle; and
   a first edge of said side port, said first edge being adjacent said rounded shoulder, said first edge being located at a distance from said modified, pencil-like point, said distance being less than about 1.5 times the external diameter of said elongated, hollow needle.

2. The spinal needle defined in claim 1 wherein said second cross sectional area of said side port is determined by the formula L×W where L represents the length of said side port and W represents the width of said side part, said second cross sectional area being greater than about said first cross sectional area which is determined by the formula $\pi D^2/4$ where D represents the diameter of said lumen.

3. The spinal needle defined in claim 2 wherein said length L is less than 1.5 times said diameter D of said lumen.

4. The spinal needle defined in claim 1 wherein said side port incrementally modifies the external profile of said elongated, hollow needle adjacent said rounded shoulder.

5. The spinal needle defined in claim 1 wherein said side port reduces a moment arm between said modified, pencil-like point and said side port by said side port being located adjacent said rounded shoulder.

6. A spinal needle for the delivery of anesthetic to the spinal column, said spinal needle being configured as an elongated, hollow needle, a lumen in said elongated, hollow needle, said lumen having a first cross sectional area, the improvement comprising:

a relatively small gauge for said hollow needle, said relatively small gauge comprising a needle gauge that is at least as small as 24 gauge;

a modified, pencil-like point on one end of said elongated, hollow needle;

a rounded shoulder on said elongated, hollow needle at the juncture of said modified pencil-like point with said elongated, hollow-needle;

a side port through a sidewall of said elongated, hollow needle, said side port providing fluid communication through said sidewall between said lumen and the exterior of said elongated, hollow needle, said side port having a second cross sectional area, said second cross sectional area being incrementally larger than said first cross sectional area; and a leading edge of said side port located adjacent said rounded shoulder, said side port being cut through said side wall to thereby modify the external profile of said elongated, hollow needle adjacent said rounded shoulder, a reduced moment arm for reduced breakage of said elongated, hollow needle, said reduced moment arm comprising said side port being located adjacent said rounded shoulder, said reduced moment arm being held to less than 1.5 times the external diameter of said elongated, hollow needle, said moment arm being measured by the distance between the midline of said port and the end of said modified, pencil-like point.

7. The spinal needle defined in claim 6 wherein said side port has a length less than 1.5 times the diameter of said lumen.

8. A method for delivering a spinal anesthesia comprising the steps of:

obtaining an elongated spinal needle, said spinal needle having a hollow lumen having an internal diameter and a first cross sectional area;

selecting a gauge for said spinal needle, said gauge being at least as small as 24 gauge;

forming a modified, pencil-like point on a distal end of said elongated spinal needle;

shaping a rounded shoulder on said elongated spinal needle at the juncture of said modified, pencil-like point with said elongated spinal needle;

preparing a side port though a side wall of said elongated hollow needle between said lumen and the ambient, said side port having a second cross sectional area, said second cross sectional area being incrementally greater than said first cross sectional area of said lumen;

placing said side port adjacent said rounded shoulder;

forming a leading edge on said side port, said leading edge being closest to said rounded shoulder, said leading edge being located less than 1.5 times the external diameter of said elongated spinal needle from the tip of said modified, pencil-like point thereby reducing a moment arm on said elongated spinal needle;

atraumatically parting the dura with said rounded shoulder by gradually stretching fibers in the dura gradually releasing said fibers upon withdrawal of said elongated spinal needle; and passing said spinal anesthesia through said lumen of said elongated spinal needle and directing said spinal anesthesis through said side port.

* * * * *